United States Patent [19]

Yamada

[11] Patent Number: 4,948,591
[45] Date of Patent: Aug. 14, 1990

[54] SOFT CAPSULAR PREPARATION OF SODIUM PICOSULFATE

[75] Inventor: Tohru Yamada, Fuji, Japan

[73] Assignee: Tokai Capsule Co., Ltd., Shizuoka, Japan

[21] Appl. No.: 344,985

[22] Filed: Apr. 28, 1989

[30] Foreign Application Priority Data

May 10, 1988 [JP] Japan ................................ 63-113311

[51] Int. Cl.$^5$ ................................................ A61K 9/48
[52] U.S. Cl. ...................................... 424/456; 424/451; 514/962
[58] Field of Search ................ 424/456, 451; 514/962, 514/963

[56] References Cited

U.S. PATENT DOCUMENTS 4,690,816 9/1987 Hata et al. ........................... 424/456

FOREIGN PATENT DOCUMENTS

| 0032825 | 7/1981 | European Pat. Off. . |
| 2548539 | 7/1984 | France . |
| 2051801A | 1/1981 | United Kingdom . |

*Primary Examiner*—Thurman K. Page
*Attorney, Agent, or Firm*—Oblon, Spivak, McClelland, Maier & Neustadt

[57] ABSTRACT

A soft capsular preparation comprising a polyethylene glycol solution of sodium picosulfate. The soft capsular preparation is stable over a prolonged storage time and is convenient to carry around. In addition, an exact dosage of the medicine can be administered.

8 Claims, No Drawings

SOFT CAPSULAR PREPARATION OF SODIUM PICOSULFATE

BACKGROUND OF THE INVENTION

1. Field of the Invention:

This invention relates to a soft capsular preparation comprising sodium picosulfate, and more particularly, to a soft capsular preparation comprising a polyethylene glycol solution of sodium picosulfate. The soft capsular preparation is stable over a prolonged storage time and is convenient to carry around. In addition, an exact dosage of the medicine can be administered.

2. Description of the Background

Sodium picosulfate [4,4,-(2-pyridilmethylene)diphenolbis(sodiumsulfate)monohydrate]is widely used as a medicine for constipation (laxative).

A sodium picosulfate preparation is commercially available in a syrupy liquid form. Conventionally, it is administered by dissolving in water when used.

Such a liquid form preparation is, however, inconvenient to carry around. In addition, the dosage must be measured every time it is administered.

There is, therefore, a need for sodium picosulfate in a solid preparation form. However, long-term storage in a solid form results in deterioration with browning or decomposition. The solid form preparation is thus accompanied by drawbacks.

In order to improve the long-term storage stability of sodium picosulfate, preparation in a soft capsular form might be suggested. Unfortunately, however, this technique is not good because sodium picosulfate, white crystal powder, is sparingly soluble in oily substances, although it is readily soluble in water.

A soft capsular preparation was developed as the most suitable preparation form capable of containing oily substances. Recently, there has been a strong desire to formulate water-soluble substances as well in soft capsular form. Various studies in this respect have been undertaken.

Conventionally known methods for incorporating water-soluble substances in a soft capsule can be roughly divided into the following three methods:

(1) A method of preparing a W/O emulsion from a water-soluble substance and an oily substance using a surface active agent. The W/O emulsion is encapsulated into a soft capsular film to prepare a soft capsular preparation.

(2) A method of preparing a suspension of an oily substance in a mixture of water-soluble substance and bees wax. The suspension is encapsulated into a soft capsular film, and changed to a semi-solid state by using thixotropy to prepare a soft capsular form.

(3) A method of having a water-soluble substance adsorbed on an adsorbent, such as a light silicate anhydride and the like, and preparing a suspension of such a light silicate anhydride in an oily solution. The suspension is encapsulated into a soft capsular film to prepare soft capsular form.

All of these conventional methods, however, have the following drawbacks.

(a) All of the above three methods necessitate a large volume of contents to be encapsulated. This makes the capsule bigger and the administration difficult.

(b) All of the above three methods require to encapsul suspensions which are opaque. In order to improve the outward appearance of the product for promoting commercial value of the product, unnecessary substances, including pigment, titanium oxide, or the like should be formulated in the capsular film.

(c) When the soft capsular agent prepared by method (1) is left under severe conditions for an extended period of time, e.g. exposed to high temperature conditions, the emulsion becomes unbalanced and the contents tend to ooze out through the capsular film.

(d) The surface film of the soft capsule prepared by method (2) gradually looses the solubility due to the influence of bees wax, resulting in a delayed degradation time.

(e) In method (3), the adsorbent used has a light density and is bulky, thus requiring an increase number of manufacturing processes and a high production cost.

In view of this situation, the present inventors have undertaken extensive studies, and found that a soft capsular preparation of sodium picosulfate which is stable for an extended period of time can be prepared by dissolving sodium picosulfate in polyethylene glycol and encapsulating the solution into a soft capsular film. This finding has led to the completion of the present invention.

SUMMARY OF THE INVENTION

Accordingly, an object of the present invention is to provide a soft capsular preparation comprising a polyethylene glycol solution of sodium picosulfate.

DETAILED DESCRIPTION OF THE INVENTION AND PREFERRED EMBODIMENTS

A soft capsular preparation of this invention is prepared by first dissolving sodium picosulfate in polyethylene glycol. Polyethylene glycol having a molecular weight of 200 to 600 and being a liquid at normal temperature is desirable. Four (4) parts by weight or more of polyethylene glycol is used per 1 part by weight of sodium picosulfate, with a particularly preferable amount being 8 to 45 parts by weight. A small amount of water, glycerol, peppermint oil, sweetener, or the like can be formulated in the content to be encapsuled, as required.

Conventional capsular films can be applied as the film for covering the content. Any method, including a seamless capsule method, a rotary method (developed by Scherer), a method using a Liner machine or an Accogel machine, and the like, can be applied for manufacturing the capsules. Also, various manufacturing machines can be used for manufacturing the capsule.

Other features of the invention will become apparent in the course of the following description of the exemplary embodiments which are given for illustration of the invention and are not intended to be limiting thereof.

EXAMPLES

EXAMPLE 1

(i) 10 kg of gelatin, 3 kg of glycerol, and 7 kg of purified water were mixed and heated at 80 C for 3 hours with stirring to prepare a gelatin sol solution. After deaerating in vacuo, the sol solution was stored at 50° C. in a thermost. The product was served as soft capsular film material.

(ii) 125 g of sodium picosulfate was added to 1 kg of polyethylene glycol 200. The mixture was heated at 80° C. for 2 hours with stirring to obtain a clear solution. A soft capsular preparation encapsulating 30mg of this solution was prepared using the soft capsular film material prepared in
(i). A conventional method using a rotary filler manufactured by Liner Co., Ltd. was employed.

EXAMPLE 2

30 g of sodium picosulfate and 270 g of glycerol were added to 1.3 kg of polyethylene glycol 400 and heated at 80° C. for 2 hours with stirring to prepare a clear solution. A soft capsular preparation encapsulating 80 mg of this solution was prepared according to the same process as in Example 1.

EXPERIMENTAL EXAMPLE 1

The soft capsule of sodium picosulfate obtained in Example 1 was tested for storage stability. The results are shown in Table 1.

TABLE 1

|  | After being left for 30 days | | |
|---|---|---|---|
| Conditions | Separation of crystals | Leakage of liquid rate (%) | Residual |
| Temperature: −10° C. Left in a glass bottle with a stopper | None | None | 100.2 |
| Temperature: 40° C. Left in a glass bottle with a stopper | None | None | 100.5 |

The soft capsular preparation of this invention has many advantages. For example, it is stable over a prolonged storage time and is convenient to carry around. In addition, an exact dosage of the medicine can be administered.

Obviously, numerous modifications and variations of the present invention are possible in light of the above teachings. It is therefore to be understood that within the scope of the appended claims, the invention may be practiced otherwise than as specifically described herein.

What is claimed is:

1. A soft capsular preparation comprising a polyethylene glycol solution of sodium picosulfate encapsulated with a capsular film.

2. The soft capsular preparation according to claim 1, wherein the ratio of polyethylene glycol/sodium picosulfate is at least 4 parts by weight of polyethylene glycol per 1 part by weight of sodium picosulfate.

3. The soft capsular preparation according to claim 2, wherein the ratio of polyethylene glycol/sodium picosulfate is 8 to 45 parts by weight of polyethylene glycol per 1 part by weight of sodium picosulfate.

4. The soft capsular preparation according to claim 1, further comprising a small amount of water, glycerol, peppermint oil, or sweetener.

5. The soft capsular preparation according to claim 1, wherein said polyethylene glycol has a molecular weight of 200 to 600 .

6. A method comprising administering to a subject the soft capsular preparation according to claim 1, as a laxative for constipation.

7. The soft capsular preparation according to claim 1, wherein said capsular film is medicinally inert.

8. The soft capsular preparation according to claim 7, wherein said capsular film consists essentially of gelatin.

* * * * *